(12) United States Patent
Konishi et al.

(10) Patent No.: US 11,224,994 B2
(45) Date of Patent: *Jan. 18, 2022

(54) METHOD FOR RECOVERING CONSTITUENT MEMBERS FROM USED ABSORBENT ARTICLE

(71) Applicant: UNICHARM CORPORATION, Ehime (JP)

(72) Inventors: Takayoshi Konishi, Kagawa (JP); Toshio Hiraoka, Kagawa (JP); Noritomo Kameda, Kagawa (JP)

(73) Assignee: Unicharm Corporation, Ehime (JP)

( * ) Notice: Subject to any disclaimer, the term of this patent is extended or adjusted under 35 U.S.C. 154(b) by 196 days.

This patent is subject to a terminal disclaimer.

(21) Appl. No.: 16/568,869

(22) Filed: Sep. 12, 2019

(65) Prior Publication Data
US 2020/0016794 A1    Jan. 16, 2020

Related U.S. Application Data

(63) Continuation of application No. PCT/JP2017/045384, filed on Dec. 18, 2017.

(30) Foreign Application Priority Data

Mar. 31, 2017    (JP) .............................. JP2017-072200

(51) Int. Cl.
*B29B 17/02* (2006.01)
*B09B 3/00* (2006.01)
*B32B 43/00* (2006.01)

(52) U.S. Cl.
CPC ............ *B29B 17/02* (2013.01); *B09B 3/0008* (2013.01); *B32B 43/006* (2013.01);
(Continued)

(58) Field of Classification Search
CPC .......... B09B 3/0008; B09B 2017/0293; B32B 43/006; Y10T 156/1111; Y10T 156/1116;
(Continued)

(56) References Cited

U.S. PATENT DOCUMENTS 5,558,745 A * 9/1996 Conway ................. D21B 1/026
162/60
6,238,516 B1 * 5/2001 Watson ................. D21B 1/026
162/8

(Continued)

FOREIGN PATENT DOCUMENTS

CN       106460327 A    2/2017
JP       2001104929 A   4/2001
(Continued)

OTHER PUBLICATIONS

International Search Report issued in corresponding International Application No. PCT/JP2017/045384, dated Feb. 6, 2018, with translation (5 pages).

*Primary Examiner* — Mark A Osele
(74) *Attorney, Agent, or Firm* — Osha Bergman Watanabe & Burton LLP

(57) ABSTRACT

A method of recovering structural members from a used absorbent article comprising a front sheet, a back sheet and an absorbent body between the front sheet and the back sheet, wherein at least one of the front sheet and the back sheet includes a film, and wherein the absorbent body includes an absorbent body material, may include swelling the used absorbent article with water, applying a physical shock to and disintegrating the swelled used absorbent article into at least the film and the absorbent body material, and separating the film and the absorbent body material.

16 Claims, 4 Drawing Sheets

(52) U.S. Cl.
CPC .. *B29B 2017/0293* (2013.01); *Y10T 156/1111* (2015.01); *Y10T 156/1116* (2015.01); *Y10T 156/1147* (2015.01)

(58) Field of Classification Search
CPC ......... Y10T 156/1147; Y10T 156/1174; Y10S 156/92; B29B 2017/0293
See application file for complete search history.

(56) References Cited

U.S. PATENT DOCUMENTS

| | | | |
|---|---|---|---|
| 7,306,697 B2* | 12/2007 | Kikushima | B29B 17/02 |
| | | | 162/4 |
| 10,533,282 B2* | 1/2020 | Konishi | D21B 1/026 |
| 10,538,878 B2* | 1/2020 | Konishi | D21B 1/10 |
| 2016/0237617 A1 | 8/2016 | Yamaguchi et al. | |
| 2017/0107667 A1 | 4/2017 | Konishi et al. | |
| 2017/0239687 A1 | 8/2017 | Ito | |
| 2017/0305037 A1 | 10/2017 | Konishi et al. | |
| 2018/0272395 A1* | 9/2018 | Herriott | B09B 3/0008 |
| 2020/0001506 A1* | 1/2020 | Konishi | B29B 17/0026 |

FOREIGN PATENT DOCUMENTS

| | | | |
|---|---|---|---|
| JP | 2002273731 A | 9/2002 | |
| JP | 2010059586 A | 3/2010 | |
| JP | 2015086483 A | 5/2015 | |
| JP | 2016079525 A | 5/2016 | |
| JP | 2016131956 A | 7/2016 | |

* cited by examiner

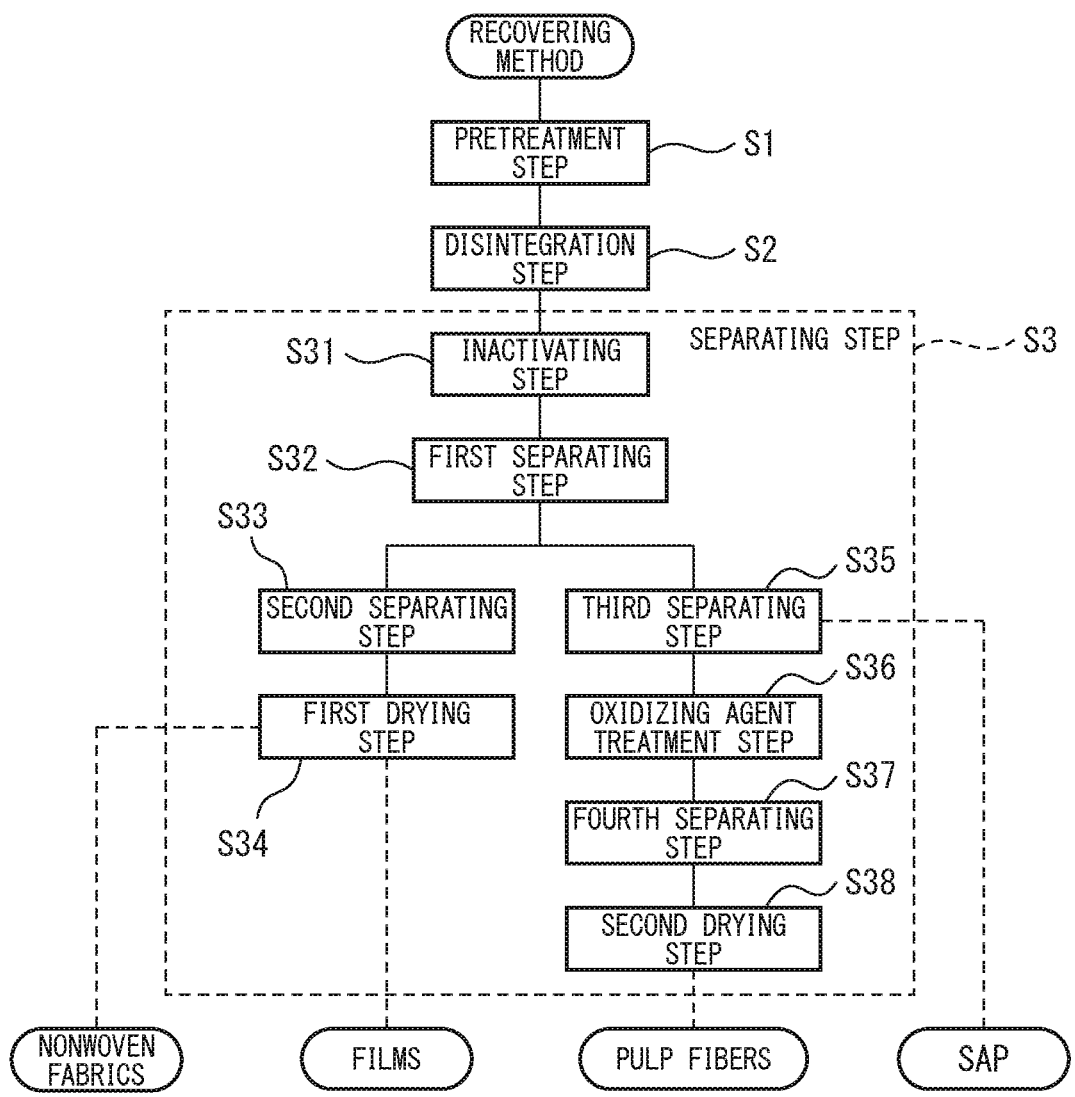

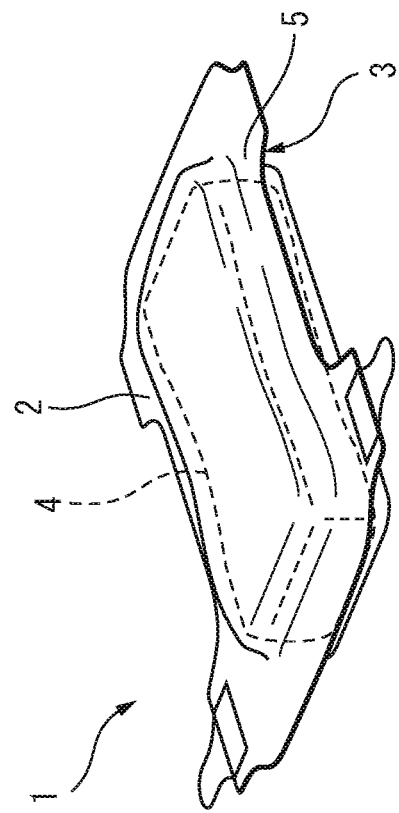
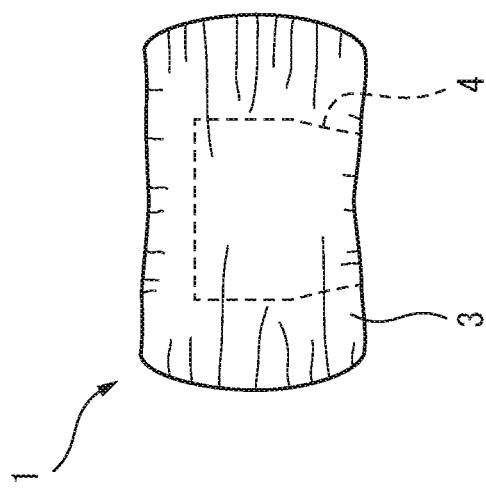

METHOD FOR RECOVERING CONSTITUENT MEMBERS FROM USED ABSORBENT ARTICLE

TECHNICAL FIELD

The present invention generally relates to a method of recovering structural members from a used absorbent article.

BACKGROUND

Techniques for recycling absorbent articles such as used disposable diapers are known. For example, Patent Literature 1 discloses a method of reutilizing used paper diapers. The method includes a step of breaking up the used paper diapers into fragments, a step of loading the broken up paper diapers into a disintegrating drum, a step of disintegrating the loaded paper diapers into pulp components (including high molecular polymers) and non-pulp components by the disintegrating drum, and a step of separating the disintegrated pulp components and non-pulp components. In the disintegrating step, the broken up paper diapers are loaded into the disintegrating drum in which industrial water and seawater have been charged, and the paper diapers in the broken up state are disintegrated into pulp components and non-pulp components by multiple projections provided on the inner wall of the rotating disintegrating drum. The non-pulp components are reutilized as regenerated resins and the like. With the pulp components, the high molecular polymers are broken up into fine particulates by a pulverizer and disposed of, while the pulp is recovered.

Patent Literature 1: Japanese Unexamined Patent Publication No. 2010-59586

According to Patent Literature 1, when the used paper diapers are disintegrated into pulp components and non-pulp components, the paper diapers are first broken up into numerous chips (fragments). However, breaking up the paper diapers into chips can potentially produce debris and pieces at the broken sections of each of the chips. In particular, it is common for the used absorbent articles to be disposed of in a rolled-up state or folded state with the front sheets on the inside, so that excreta are not exposed on the front side, and so that odor does not diffuse to the surroundings. With used absorbent articles, therefore, production of debris is highly likely to occur since the locations where the articles are broken and the shapes of the broken sections are not consistent. Furthermore, when such chips are disintegrated in a disintegrating drum, additional debris may be produced from the broken sections of each chip due to the shock of rotation of the disintegrating drum. The debris mixes with the drainage, making it difficult to recover. In addition, with smaller sizes of the chips, the sizes of the pulp components and the sizes of the non-pulp components in them become more uniform and more difficult to distinguish, thus potentially interfering with separation between the components. This results in a lower recovery rate for the structural members such as films in the paper diapers or other absorbent articles.

SUMMARY

One or more embodiments provide a method in which, for recycling of structural members of a used absorbent article which includes a front sheet, a back sheet and an absorbent body situated between the front sheet and the back sheet, with at least one of the front sheet and the back sheet including a film as a structural member and the absorbent body including an absorbent body material as a structural member, it is possible to efficiently recover the structural members from the used absorbent article without breaking up the used absorbent article.

The method of recovering structural members from a used absorbent article according to one or more embodiments may be a method of recovering structural members from a used absorbent article which includes a front sheet, a back sheet and an absorbent body situated between the front sheet and the back sheet, wherein at least one of the front sheet and the back sheet includes a film and the absorbent body includes an absorbent body material, the method comprising: swelling the used absorbent article with water; applying a physical shock to and disintegrating the used absorbent article into at least the film and the absorbent body material; and separating the film and the absorbent body material.

In the pretreatment step of a method of one or more embodiments, a used absorbent article is allowed to absorb water while in its original form without breakup, and also without inactivation of the superabsorbent polymer. Therefore, the used absorbent article can be caused to absorb water up to nearly the maximum absorption of the used absorbent article (for example, up to a maximum absorption of 80 mass % or greater). In other words, the used absorbent article can be brought to a highly expanded state with water. A very high internal pressure is produced inside the used absorbent article as a result. The internal pressure allows the used absorbent article to be converted to a flat expanded state in water, from the rolled-up state or folded state after it has been disposed of. Since the used absorbent article is highly expanded at this time, some portions of the surface become prone to rupture.

In the subsequent disintegration step of one or more embodiments, the used absorbent article which has thus been expanded flat and has some locations of the surface prone to rupture due to the expansion is subjected to physical shock, such as shock by a method of repeatedly raising it from the base section and then dropping it down to cause impact onto the base section. As a result, since further shock is applied to the used absorbent article whose surface is prone to rupture at some locations, the surface rupture (detach) allowing the interior absorbent body material of the used absorbent article to effuse out (fly out) through the torn section in the absorbent body material. This allows the used absorbent article to disintegrate into at least the film and absorbent body material. During this time, except for some partial cracking, the film maintains approximately the same shape as when it was in the absorbent article, or in other words, its original shape. Compared to being broken up into fragments before disintegration, therefore, the size, shape and mass of the film are distinctly different from the size and shape of the absorbent body material, thus allowing the film to be easily separated from the absorbent body material in the subsequent separating step as well.

This will allow the structural members such as a film to be separated from the other structural members while maintaining their shapes without breaking up. The structural members, such as a film, of the absorbent article can therefore be efficiently recovered.

The method of one or more embodiments may also be the method above, wherein the absorbent body material includes a superabsorbent polymer and pulp fibers, and method further comprises inactivating the superabsorbent polymer in an acidic aqueous solution containing an inactivating agent, before the separating of the film and the absorbent body material, and wherein in the separating of the film and the absorbent body material, the film is separated from a mixture containing the pulp fibers, the inactivated superabsorbent polymer, and any waste water discharged from the inactivation of the superabsorbent polymer.

The superabsorbent polymer before inactivation is in a highly viscous state and cannot be considered to be easily separable from a film. In the method of one or more embodiments, therefore, the superabsorbent polymer is inactivated before the film and absorbent body material are separated, thus dewatering the superabsorbent polymer. Since this can lower the viscosity of the superabsorbent polymer, it is possible to easily separate the film from the superabsorbent polymer, and therefore from the mixture containing the pulp fibers. The structural members, such as a film, of the absorbent article can therefore be efficiently recovered.

The method of one or more embodiments may also be a method discussed above, wherein in the disintegrating of the swelled used absorbent article, the swelled used absorbent article is loaded into a horizontal-axis rotary drum, and the physical shock is applied to the swelled used absorbent article by rotating the rotary drum, raising the swelled used absorbent articles from a lower area that is further downward in a vertical direction inside the rotary drum to an upper area that is further upward, and allowing the swelled used absorbent article to fall by gravity from the upper area to the lower area and physically impact an inner wall of the rotary drum in the lower area.

In one or more embodiments, a horizontal-axis rotary drum that rotates around an imaginary rotation axis extending in the horizontal direction (for example, a rotary drum in the washing tank of a horizontal-axis washing machine) may be used to continuously and stably apply physical shock to the used absorbent article. That is, the used absorbent article set on the inner wall of the rotary drum is raised up from the lower area to the upper area in the rotary drum by rotation of the rotary drum and then fall down by gravity from the upper area to the lower area, impacting it with the inner wall of the lower area to allow shock to be applied to the used absorbent article. By continuing rotation of the rotary drum, the shock of the impact can be stably, continuously and easily applied. This allows the joining section between the front sheet (a nonwoven fabric or film) and the back sheet (a film) of the used absorbent article to be stably torn (detached), and allows the used absorbent article to be reliably disintegrated into films and absorbent body material.

The method of one or more embodiments may be a method discussed above, wherein in the swelling of the used absorbent article, the water is at a temperature between 70° C. to 98° C.

In one or more embodiments, the water temperature is 70° C. or higher to allow the adhesive joining the film and other members to be softened by the heat of the water to lower the bonding force of the adhesive. Furthermore, limiting the water temperature to no higher than 98° C. can ensure that the water is present as a liquid, thus allowing the water to be reliably absorbed into the used absorbent article. This can more reliably generate a state in which the surface is prone to rupture by expansion, and can generate a state in which the bonding force of the adhesive is reduced. In the disintegration step, therefore, the joining section between the front sheet (a nonwoven fabric or film) and the back sheet (a film) which has reduced bonding force become torn (detached), allowing the absorbent body material inside the used absorbent article to effuse out (fly out) through the torn section. This allows the used absorbent article to more reliably disintegrate into at least the film and absorbent body material. Sterilization is also extremely important for reutilization of used absorbent article. By setting the water temperature to 70° C. or higher, an effect of sterilization (disinfection) can also be exhibited.

The method of one or more embodiments may also be a method discussed above, wherein the swelled used absorbent article contains the water in an amount of 90 mass % or greater of a maximum absorption of the used absorbent article.

In one or more embodiments, the pretreatment step has a step of causing the used absorbent article to absorb water in an amount of 90 mass % or greater of the maximum absorption of the used absorbent article. In other words, the used absorbent article can be brought to a maximally expanded state with water. As a result, a very high internal pressure can be produced in the used absorbent article. In the disintegration step, the physical shock applied to the used absorbent article by the internal pressure allows the joining section between the front sheet (a nonwoven fabric or film) and the back sheet (a film) to be more reliably torn (detached), so that the absorbent body material inside the used absorbent article can effuse out (fly out) through the torn section.

The method of one or more embodiments may also be a method discussed above, wherein the film and the absorbent body material are connected at joining sections by an adhesive, and wherein in the separating of the film and the absorbent body material, the adhesive at the joining sections is removed by dissolving the adhesive with a solvent.

In one or more embodiments, the adhesive at the joining sections between the film (for example, a back sheet film) and other members (for example, a front sheet film or nonwoven fabric, and an absorbent body material) are removed with a solvent, thus allowing the film and the other members to be separated from each other without breaking up and while maintaining their shapes. The structural members, such as a film, of the absorbent article can therefore be efficiently recovered. Moreover, the film and other members can be separated without leaving the adhesive in the film. This allows the film to be reusable as highly pure resin and can minimize adverse effects of the adhesive when the film is reutilized.

The method of one or more embodiments may also be a method discussed above, wherein the solvent includes at least one terpene selected from a group consisting of terpene hydrocarbon, terpene aldehyde and terpene ketone.

The method of one or more embodiments can more reliably dissolve the adhesive by using a terpene as the solvent to dissolve the adhesive. In addition, because terpenes have a high washing effect for contaminating oils, it also allows decomposition and removal of other oil components (such as printing inks) when such oil components are present in the used absorbent article. This allows the film to be reusable as highly pure resin.

The method of one or more embodiments may also be a method discussed above, wherein in the separating of the film and the absorbent material, the film is heat-dried to remove the solvent, after the adhesive at the joining sections has been removed.

Sterilization is extremely important for reutilization of used absorbent article. In one or more embodiments, the separated film is subjected to heat-drying, i.e. it is dried in a high-temperature atmosphere or with hot air, making it possible to not only vaporize off and remove the residual solvent on the surface of the film, but to also sterilize the film with the high-temperature atmosphere or hot air. This can remove the solvent while exhibiting an effect of sterilization (disinfection), and also allows efficient recovery of the structural members such as a film of the absorbent article of one or more embodiments.

The method one or more embodiments may also be a method discussed above, wherein in the separating of the film and the absorbent body material, the pulp fibers are separated from the separated mixture, and the separated pulp fibers are treated with an aqueous solution of an oxidizing agent, wherein the reducing agent reduces a molecular weight of any residual superabsorbent polymer remaining in the pulp fibers, thereby solubilizing and removing the residual superabsorbent polymer.

In one or more embodiments, the superabsorbent polymer remaining in the pulp fibers can be solubilized and removed by oxidation using an oxidizing agent (such as ozone), thus allowing recovery of highly pure pulp fibers having a low mixing ratio of superabsorbent polymer. Therefore, the structural members of the absorbent article of one or more embodiments can be efficiently recovered.

The method of one or more embodiments may also be a method discussed above, wherein the used absorbent article is at least one selected from a group consisting of a paper diaper, a urine-absorbing pad, a sanitary napkin, a bed sheet and a pet sheet.

The method of one or more embodiments may be applied to at least a paper diaper, a urine-absorbing pad, a sanitary napkin, a bed sheet and a pet sheet, as the used absorbent article.

According to a method of one or more embodiments, it is possible, when recycling the structural members of the used absorbent article, to efficiently recover the structural members such as a film from the used absorbent article without breaking up the used absorbent article.

BRIEF DESCRIPTION OF THE DRAWINGS

FIG. 1 is a flow chart showing a method of one or more embodiments.

FIGS. 2A-B are schematic diagrams showing an example of a change of state of a used absorbent article in the pretreatment step of FIG. 1.

DETAILED DESCRIPTION

Figure 3A:
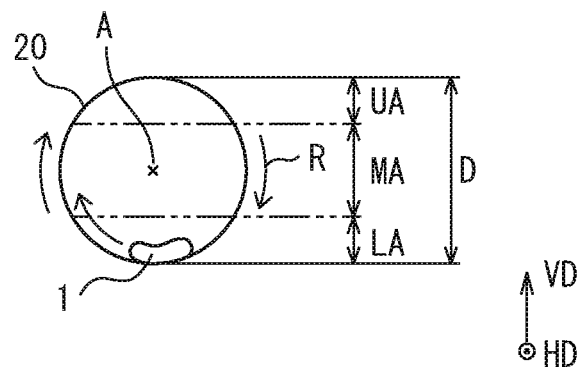
FIGS. 3A-C are schematic diagrams showing an example of a disintegration process in a disintegration step of FIG. 1.

Embodiments of the present invention will now be described. A "used absorbent article" is an absorbent article that has been used by a user, and usually it is an absorbent article in a state of having absorbed liquid excreta from the user. For one or more embodiments, however, a used absorbent article may be an absorbent article that that have been used but have not absorbed excreta, as well as an unused one.

An example of the construction of an absorbent article of one or more embodiments will now be described. The absorbent article includes a front sheet, a back sheet and an absorbent body situated between the front sheet and back sheet. The absorbent article may be a paper diaper, a urine-absorbing pad, a sanitary napkin, a bed sheet or a pet sheet, for example. The front sheet, back sheet and absorbent body are formed of structural members such as nonwoven fabrics, films, pulp fibers and superabsorbent polymers, and they are joined together by an adhesive. An example of the size of an absorbent article is a length of about 15 to 100 cm and a width of 5 to 100 cm.

The structural member of the front sheet of one or more embodiments may be a nonwoven fabric or film, for example, and specifically this includes liquid-permeable nonwoven fabrics, synthetic resin films having liquid permeation holes, and composite sheets of the same. The structural member of the back sheet may also be a nonwoven fabric or film, for example, and specifically this includes liquid-impermeable nonwoven fabrics, liquid-impermeable synthetic resin films, and composite sheets of nonwoven fabrics and synthetic resin films. The materials of the nonwoven fabric or synthetic resin film are not restricted so long as they can be used as absorbent articles, and examples include olefin-based resins such as polyethylene and polypropylene, polyamide-based resins such as 6-nylon and 6,6-nylon, and polyester-based resins such as polyethylene terephthalate (PET) and polybutylene terephthalate (PBT).

For one or more embodiments, at least one of the front sheet and back sheet of the absorbent article include a film as a structural member, but the following explanation will assume that the absorbent article has a film as the structural member of the back sheet and a nonwoven fabric as the structural member of the front sheet.

The back sheet of one or more embodiments may also include a gas-permeable outer sheet on the side opposite from the absorbent body in the thickness direction. The structural member used for the outer sheet may be the same type of structural member as the back sheet. The outer sheet is joined to the back sheet by an adhesive. The front sheet may also include a water-repellent side sheets on both outer sides in the widthwise direction. The structural member of each side sheet may be a water-repellent treated nonwoven fabric or gas-permeable synthetic resin film. The side sheet is joined to the front sheet by an adhesive. For one or more embodiments, when an outer sheet or side sheet is included in the absorbent article, the film may also include an outer sheet or side sheet.

When liquid permeability or gas-permeability is to be imparted to the film serving as the structural member, i.e. when the film is to be made porous, a filler (inorganic filler) may be added to the film. Pores are thus formed in the film by detachment occurring at the interface between the resin and filler of the film. The filler material is not particularly restricted so long as it can be used as an absorbent article, and examples include calcium carbonate, barium sulfate, calcium sulfate, barium carbonate, zinc oxide, magnesium oxide, titanium oxide, talc, silica, clay, kaolin, alumina, mica, and combinations of at least two or more of these. The filler content of a film material determines the moldability and stretchability of the film material and the moisture permeability, gas permeability and strength of a porous film obtained from it.

The structural member of the absorbent body of one or more embodiments may be the absorbent body material, i.e. pulp fibers and the superabsorbent polymer. Pulp fibers are not particularly restricted so long as they can be used as an absorbent article, and cellulosic fibers are an example. Examples of cellulosic fibers include wood pulp, crosslinked pulp, nonwood pulp, regenerated cellulose and semi-synthetic cellulose. The superabsorbent polymer (SAP) is not particularly restricted so long as it can be used in an absorbent article, and examples are polyacrylic acid salt-based, polysulfonic acid salt-based and maleic anhydride salt-based water-absorbent polymers.

One side and the other side of the absorbent body of one or more embodiments are joined to the front sheet and back sheet, respectively, via an adhesive. The portion (perimeter edge portion) of the front sheet that extends out from the absorbent body to surround the absorbent body, as viewed flat, is joined to the portion (perimeter edge portion) of the back sheet that extends out from the absorbent body to surround the absorbent body so as to surround the absorbent body, with an adhesive. The absorbent body is thus wrapped inside a joined structure between the front sheet and the back sheet. The adhesive is not particularly restricted so long as it can be used in an absorbent article and has its bonding force lowered when softened by warm water as described below, and an example is a hot-melt adhesive. Examples of hot-melt adhesives include types based mainly on rubber, such as styrene-ethylene-butadiene-styrene, styrene-butadiene-styrene and styrene-isoprene-styrene, and pressure-sensitive adhesives or heat-sensitive adhesives based mainly on olefins such as polyethylene.

The method of recovering structural members from a used absorbent article according to one or more embodiments will now be described in detail. For one or more embodiments, a used absorbent article is recovered, collected or acquired from an external source for reutilization (recycling). Also for one or more embodiments, the individual used absorbent article is recovered in a rolled-up state or folded state with the excreta-discharged front sheet on the inside, so that excreta are not exposed on the front side, and so that odor does not diffuse to the surroundings. However, the used absorbent article of one or more embodiments may not need to be in a rolled-up state or the like.

FIG. 1 is a flow chart showing the method of one or more embodiments of recovering structural members from a used absorbent article. The method of one or more embodiments includes a pretreatment step S1 of swelling a used absorbent article with water, a disintegration step S2 of applying physical shock to the swelled used absorbent article to disintegrate the used absorbent article into at least a film and an absorbent body material, and a separating step S3 of separating the disintegrated film and absorbent body material. Each of the steps will now be explained.

In the pretreatment step S1 of one or more embodiments, used absorbent articles are allowed to absorb water and swell while still in the state in which they were recovered from the external source, i.e. without destruction or tearing and while still in any rolled-up or folded state (in other words, in their original form), and also without inactivation of the superabsorbent polymer of the absorbent body. For one or more embodiments, however, the used absorbent articles are either allowed to absorb warm water to swell, or after they have absorbed water and swelled, the absorbed water is heated to produce warm water. Warm water is water at a higher temperature than ordinary temperature (20° C.±15° C., or 5 to 35° C.: JIS Z 8703).

Usually, the amount of liquid excreta actually absorbed into a used absorbent article is much smaller than the maximum absorption amount of which the absorbent article is capable of absorbing (for example, the maximum absorption amount of about 10 to 20 mass %). For one or more embodiments, by immersing each used absorbent article in warm water in the pretreatment step S1, it is caused to absorb water up to nearly the maximum absorption amount of the used absorbent article (for example, to the maximum absorption amount of 80 mass % or greater). Alternatively, each used absorbent article is immersed in water at ordinary temperature to cause absorption of water up to nearly the maximum absorption amount of the used absorbent article, and then the entire used absorbent article is heated to the warm water temperature. This allows the used absorbent article to be brought to a highly expanded state by the warm water or ordinary temperature water (hereunder also referred to simply as "warm water"). A very high internal pressure is produced inside the used absorbent article as a result. The purpose of using warm water as the water is primarily to weaken the adhesive force of the adhesive, as explained below.

FIGS. 2A-B are schematic diagrams showing an example of a change of state of a used absorbent article in the pretreatment step S1 of FIG. 1. FIG. 2A shows the state of the used absorbent article before immersion in warm water, and FIG. 2B shows the state after immersion in warm water. As shown in FIG. 2A, the used absorbent article 1 is initially in a rolled-up or folded state with the back sheet 3 on the outer side (hiding the front sheet 2 on the inner side). By immersing the used absorbent article 1 in warm water while in this state, the absorbent body 4 of the used absorbent article 1 absorbs warm water and expands while in the warm water. The internal pressure of the used absorbent article 1 gradually increases as a result. The internal pressure produces a force which acts on the used absorbent article 1, causing it to open outward. As a result, as shown in FIG. 2B, the used absorbent article 1 in the rolled-up or folded state opens outward to an approximately flat state, exposing the front sheet 2. In other words, the used absorbent article 1 can be brought to a flat expanded state in the warm water. Since the absorbent body 4 of the used absorbent article 1 is highly expanded at this time, having absorbed a large amount of warm water, it is highly prone to rupture at the surfaces, i.e. at locations on the front sheet 2 and back sheet 3 that are enveloping the absorbent body 4. In other words, the pretreatment step S1 allows the used absorbent article to be brought into a state where some of the surfaces are prone to tearing and rupture. Incidentally, if the used absorbent article 1 is initially in a flat expanded state, some locations on the surface in that state will already be in a state that is highly prone to rupture. This state cannot be produced when the used absorbent article of Patent Literature 1, for example, is broken up.

Moreover, when the used absorbent article of one or more embodiments is immersed in warm water and/or absorbs warm water, the adhesive (such as a hot-melt adhesive) used for joining between each of the structural members is softened by the heat of the warm water, thus lowering the bonding force of the adhesive. For example, the adhesive joining the perimeter edge portion of the front sheet with the perimeter edge portion of the back sheet can be softened by the heat of the warm water, thus lowering the bonding force of the adhesive. In addition, the adhesive joining the front sheet and the absorbent body and the adhesive joining the back sheet and the absorbent body can be softened by the heat of the warm water, thus lowering the bonding force of those adhesives.

In the pretreatment step S1 of one or more embodiments, as described above, expansion of the absorbent body of the used absorbent article can produce a state in which some locations of the surface of the used absorbent article are prone to rupture, and a state with lower bonding force of the adhesive. If the used absorbent article is in such a state, the used absorbent article can be reliably disintegrated in the subsequent disintegration step.

The temperature of the warm water in the pretreatment step S1 of one or more embodiments is not particularly restricted so long as the adhesive in the used absorbent article can be softened, and it may be 60° C. or higher, for example, and is 70° C. to 98° C. In other words, the pretreatment step S1 includes a step of causing the used absorbent article to swell with warm water at 70° C. to 98° C. If the temperature of the warm water is 70° C. or higher, the adhesive joining the film (a back sheet, for this embodiment) and other members (a nonwoven fabric of the front sheet or an absorbent body material of the absorbent body, for this embodiment) can be softened by the heat of the warm water, thus allowing the bonding force of the adhesive to be further lowered. Furthermore, limiting the temperature of the warm water to no higher than 98° C. can ensure that the warm water is present as a liquid, thus allowing the warm water to be more reliably absorbed into the used absorbent article. Expansion of the absorbent body and heating with warm water can more reliably produce a state in which the surfaces of the used absorbent article are prone to rupture, and a state with lower bonding force of the adhesive. The temperature of the warm water may be 75° C. to 90° C. The temperature of the warm water may be 75° C. to 85° C. Measurement of the temperature may be measurement of the warm water temperature when the used absorbent article is immersed, or it may be measurement of the temperature within 5 mm inward from the surface of the used absorbent article that has absorbed the water up to nearly their maximum absorption amount (by insertion of the tip of a temperature sensor).

In one or more embodiments, sterilization of structural materials is also extremely important for reutilization of used absorbent articles. The warm water temperature may be set to 70° C. or higher to allow an effect of sterilizing (disinfecting) the used absorbent articles to be exhibited.

The treatment time in the pretreatment step S1 of one or more embodiments, i.e. the time for immersion of the used absorbent articles in the warm water, is not particularly restricted so long as the absorbent bodies of the used absorbent articles can expand, and it may be 2 to 60 minutes, for example, or 4 to 30 minutes. If the time is too short the absorbent bodies will not be able to expand sufficiently, and if the time is too long the treatment cost will be wastefully and unnecessarily increased.

The amount of warm water absorbed by the absorbent body in the pretreatment step S1 of one or more embodiments is not particularly restricted so long as the absorbent body can expand to a degree allowing the used absorbent article to disintegrate in the subsequent disintegration step, and it may be, for example, 80 mass % or greater, and 90 mass % or greater, of the maximum absorption amount of the used absorbent article. In other words, the pretreatment step S1 includes a step of causing the used absorbent article to absorb warm water (water) in an amount of 90 mass % or greater of the maximum absorption amount of the used absorbent article. This will allow the used absorbent article to be brought to the maximally expanded state with the water. As a result, a very high internal pressure can be produced in the absorbent body of the used absorbent article. If the used absorbent article is in a folded state, the very high internal pressure allows the used absorbent article to expand very easily into their flat state. At the same time, expansion of the absorbent body allows a rupture-prone state to be even more reliably produced at the surfaces of the used absorbent article. As a result, the used absorbent article can be more reliably disintegrated by physical shock applied to the used absorbent article in the subsequent disintegration step.

The maximum absorption amount of one or more embodiments is measured by the following procedure.

(1) An unused absorbent article is dried in an atmosphere of 100° C. or higher and the mass of the absorbent article is measured.

(2) When a stretchable material forming a pocket so that water is less likely to reach the absorbent body (for example, a leg or waist stretching member) is disposed in the absorbent article, notches are formed in the stretching member to flatten the absorbent article.

(3) The absorbent article is immersed in a water bath filled with a sufficient amount of tap water, with the front sheet facing downward, and it is left for 30 minutes.

(4) After being left, the absorbent article is placed on a net with the front sheet facing downward and drained for 20 minutes, after which the mass of the absorbent article is measured.

The difference in mass before and after immersion in the tap water is defined as the maximum absorption amount.

In addition, if all of the used absorbent articles are caused to absorb warm water up to approximately the maximum absorption amount of the used absorbent articles, then the weight per used absorbent article can be approximately the same for all of the used absorbent articles (if the used absorbent articles are of the same type). Therefore, the weight of all of the used absorbent articles may be divided by the weight per used absorbent article to estimate the total number of used absorbent articles collected, if the number was unknown when the disposable absorbent articles were collected. This allows the recovery amounts of each of the structural members to be estimated. For example, the number of films to be recovered and the amount of adhesive to be treated can be estimated from the total number of used absorbent articles that were collected. Therefore, the amount of treatment solution for treatment of each of the separate structural members in the steps following the pretreatment step S1 can be easily estimated, so that they can be easily prepared.

In the subsequent disintegration step S2 of one or more embodiments, physical shock is applied to the used absorbent articles that have expanded and swelled by the pretreatment step S1, thus disintegrating the used absorbent articles into at least films (back sheets) and absorbent body materials (absorbent bodies). For one or more embodiments, the disintegration is into films (back sheets), nonwoven fabrics (front sheets) and absorbent body materials (absorbent bodies).

As a result of pretreatment step S1 of one or more embodiments, the used absorbent articles expand to become flat, with some locations of the surfaces becoming prone to rupture by the expansion, and for one or more embodiments, in particular, the bonding force of the adhesive is lowered by the heat of the warm water. In disintegration step S2, therefore, physical shock is applied to the used absorbent articles to cause some locations on the surfaces to rupture, especially at the joining sections between the front sheets (nonwoven fabrics) and back sheets (films) where the bonding force has been lowered. This allows the joining sections to become torn (detached). The physical shock is not particularly restricted, and for example, it may be a method of beating the used absorbent articles onto a surface made of a harder material than the used absorbent articles, or a method of pressing the used absorbent articles from both sides while passing them between a pair of mutually facing rolls. Even if the water in which the used absorbent articles are immersed in the pretreatment step S11 is at ordinary temperature, the used absorbent articles can be caused to expand and the surfaces made prone to rupture, and even if the atmosphere in which shock is applied to the used absorbent articles in disintegration step S12 is at ordinary temperature, the used absorbent articles can be caused to rupture (tear) at some locations on the surfaces.

Figure 3B:
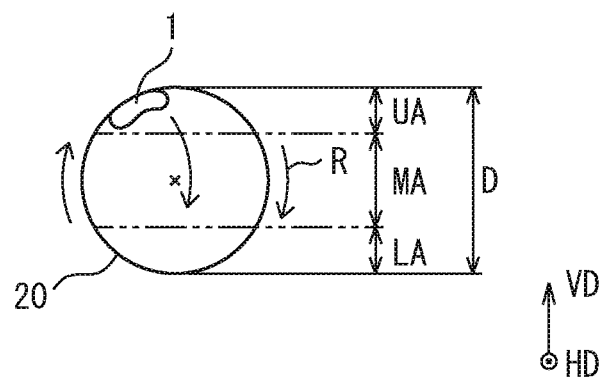
Figure 3C:
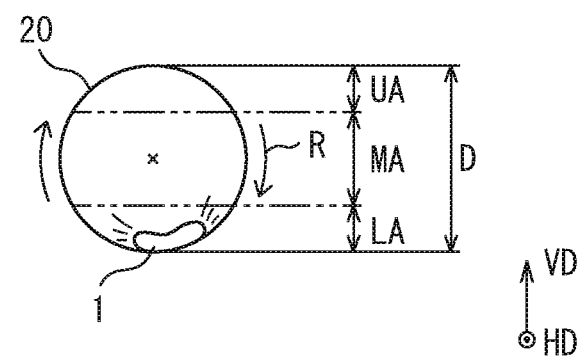

For one or more embodiments, the following method is employed as an example of a method of beating a used absorbent article on a surface made of a harder material than the used absorbent article. FIGS. 3A-C are schematic diagrams showing an example of the disintegration process in the disintegration step S2 of FIG. 1. FIGS. 3A-C show the method of applying physical shock to the used absorbent article 1. Specifically, the disintegration step S2 includes a loading step of loading the swelled used absorbent article 1 into a rotary drum 20, and a shock step of applying physical shock to the used absorbent article 1 by rotation of the rotary drum 20.

As shown in FIG. 3A, the rotary drum 20 of one or more embodiments is a horizontal-axis rotary drum that rotates (R) around an imaginary rotation axis A extending in the horizontal direction HD. The rotary drum 20 may be a rotary drum in the washing tank of a horizontal-axis washing machine, for example, and therefore the disintegration step S2 may be carried out using a horizontal-axis washing machine. The horizontal-axis washing machine used may be an ECO-22B by Inax Corp., for example. The rotary drum 20 has a lower area LA that is further downward and an upper area UA that is further upward, in the vertical direction VD, and a center area MA between the lower area LA and the upper area UA. The lower area LA may be an area of D/3 and an area of D/4 at the lower end in the vertical direction VD of the rotary drum 20, where D is the inner diameter of the rotary drum 20. The upper area UA may be an area of D/3 and an area of D/4 at the upper end in the vertical direction VD of the rotary drum 20. The inner diameter D×depth may be 50 to 150 cm×30 to 120 cm, for example.

In the loading step, as shown in FIG. 3A, the used absorbent articles 1 are set on the inner wall of the rotary drum 20 in the lower area LA. During this time, the total number of the used absorbent articles 1 that are set is a number in an amount that allows sufficient shock to be applied to the used absorbent articles 1 in the shock step, and at maximum it is the number that fills the lower area LA. If the number is too large, movement of the used absorbent articles in the rotary drum 20 will be minimal, and it may not be possible to apply shock to the used absorbent articles.

In the subsequent shock step of one or more embodiments, as shown in FIG. 3B, the rotary drum 20 is rotated to lift the used absorbent articles 1 from the lower area LA to the upper area UA in the rotary drum 20. Also, as shown in FIG. 3C, the used absorbent articles 1 fall by gravity from the upper area UA to the lower area LA, thus impacting with the inner wall of the rotary drum 20 in the lower area LA. This step allows physical shock to be applied to the used absorbent articles 1.

The rotational speed of the rotary drum 20 of one or more embodiments is not particularly restricted so long as it allows the shock step to be carried out, and it may be 30 times/min to 100 times/min, for example. The temperature of the used absorbent articles 1 is also kept at a relatively high temperature by the warm water absorbed into the used absorbent articles 1, but the temperature of the atmosphere in the rotary drum 20 may be 70° C. or higher and 75° C. or higher, from the viewpoint of minimizing reduction in the temperature of the adhesive and maintaining a sterilizing effect. The temperature in the rotary drum 20 may be no higher than 98° C. and no higher than 90° C. from the viewpoint of handling the used absorbent articles 1. The amount of water in the rotary drum 20 may be as small as possible, and it is small enough so that at least the used absorbent articles 1 are not lower than the water surface in the shock step. If the used absorbent articles 1 are lower than the water surface, the shock to the used absorbent articles 1 will be absorbed by the water, making it difficult to apply the intended shock to the used absorbent articles 1.

The treatment time during the shock step of one or more embodiments, i.e. the time for rotation of the rotary drum 20, is not particularly restricted so long as the front sheets 2 and back sheets 3 and the absorbent body materials can be disintegrated, and it may be 2 to 40 minutes, for example, and may be 4 to 20 minutes.

Figure 4:
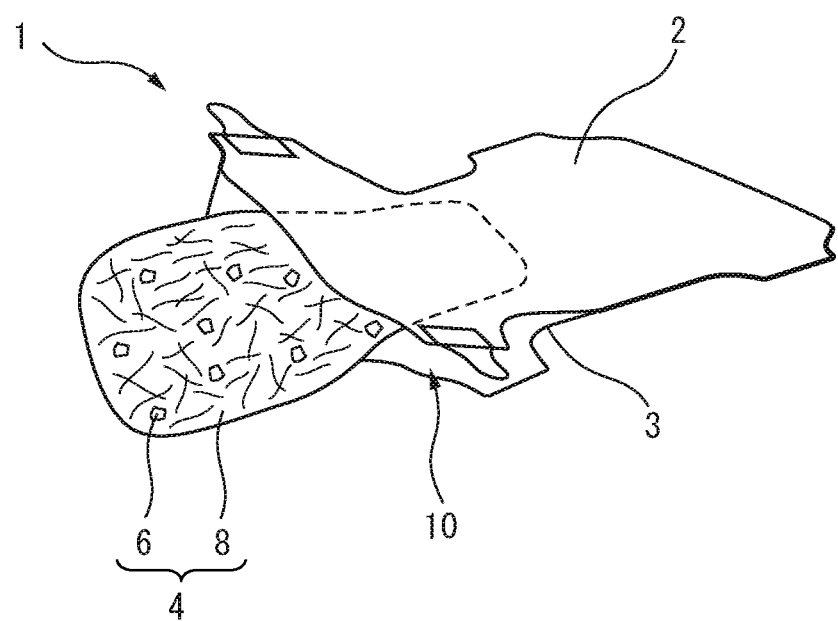
FIG. 4 is a schematic diagram showing an example of a used absorbent article which has disintegrated in the disintegration step of FIG. 1.

FIG. 4 is a schematic diagram showing an example of the used absorbent article 1 that has disintegrated in the disintegration step of FIG. 1. The joining section between the front sheet 2 (nonwoven fabric) and the back sheet 3 (film) of the used absorbent article 1 is ruptured and torn by the physical shock. At the same time, the absorbent body material (pulp fiber 8 and water-absorbent polymer 6) of the used absorbent article 1 effuse out (fly out) through the torn section 10 by internal pressure of the absorbent body 4. This allows the used absorbent article 1 to disintegrate into the front sheet 2 (nonwoven fabric) and back sheet 3 (film) and the absorbent body material (pulp fiber 8 and water-absorbent polymer 6).

For one or more embodiments, shock can be applied to the used absorbent article 1 by beating of the used absorbent article 1 by gravity from the upper area UA toward the lower area LA using the horizontal-axis rotary drum 20. By continuing rotation of the rotary drum 20, it is possible to easily apply such shock in a stable and continuous manner. This allows the joining section between the front sheet 2 (nonwoven fabric) and back sheet 3 (film) of the used absorbent article 1 to be more stably torn (detached), and allows the used absorbent article 1 to be reliably disintegrated into the film and the absorbent body material. An existing type of washing machine may be used.

Next, in the separating step S3 of one or more embodiments, the disintegrated films (back sheets) and absorbent body materials (pulp fibers and water-absorbent polymer) are separated. For one or more embodiments, the different films (back sheets) and nonwoven fabrics (front sheets) are separated from the absorbent body materials (pulp fibers and water-absorbent polymer). However, the nonwoven fabrics may also be joined to films. During this time, the front sheets (nonwoven fabrics) and back sheets (films) essentially maintain their original shapes, i.e. the same shapes as when they were in the absorbent articles. Compared to being broken up into fragments before disintegration, therefore, the sizes, shapes and masses of the front sheets (nonwoven fabrics) and back sheets (films) are distinctly different from the sizes and shapes of the absorbent body materials. In the separating step S3 of one or more embodiments, therefore, the front sheets (nonwoven fabrics) and back sheets (films) can be easily separated from the absorbent body materials (pulp fibers and water-absorbent polymer). The separating method of one or more embodiments may be, for example, a method of using a screen through which the absorbent body materials pass but the front sheets and back sheets do not pass. This will allow the structural members such as films to be separated from the other structural members while maintaining their shapes without breaking up. The structural members, such as films, of the absorbent articles can therefore be efficiently recovered.

For one or more embodiments, the separating step S3 may include an inactivating step S31 of inactivating the superabsorbent polymer in an aqueous solution containing an inactivating agent before separating the films and absorbent body materials, and a first separating step S32 of separating the films from a mixture containing the pulp fibers, the inactivated superabsorbent polymer and waste water discharged from the superabsorbent polymer by inactivation.

In the inactivating step S31 of one or more embodiments, prior to the first separating step S32, the front sheets (nonwoven fabrics), the back sheets (films) and the absorbent body materials (pulp fibers and superabsorbent polymer) are immersed in an aqueous solution containing an inactivating agent that can inactivate the superabsorbent polymer. This allows inactivation of the superabsorbent polymer adhering to the front sheets, the back sheets and the pulp fibers. It is thus possible to convert the superabsorbent polymer which was in a highly viscous state before inactivation, into superabsorbent polymer in a low-viscosity state, due to dewatering by inactivation.

The inactivating agent of one or more embodiments is not particularly restricted, and it may be an inorganic acid, an organic acid, lime, calcium chloride, magnesium sulfate, magnesium chloride, aluminum sulfate, aluminum chloride or the like. Inorganic acids and organic acids may be among these because they do not leave residue of ash in the pulp fibers. When an inorganic acid or organic acid is used as the inactivating agent, the pH of the inorganic acid aqueous solution or organic acid aqueous solution is no higher than 2.5 and may be 1.3 to 2.4. The aqueous solution containing the inactivating agent may therefore be considered to be an acidic aqueous solution. If the pH is too high, it may not be possible to sufficiently lower the water-absorbing capacity of the superabsorbent polymer. The sterilizing power can also be potentially lowered. If the pH is too low there will be a risk of corrosion of the equipment, and large amounts of alkaline chemicals will be necessary for neutralizing treatment during waste water treatment. Examples of inorganic acids include sulfuric acid, hydrochloric acid and nitric acid. The inorganic acids may include sulfuric acid from the viewpoint of cost and the absence of chlorine. Organic acids include citric acid, tartaric acid, glycolic acid, malic acid, succinic acid, acetic acid and ascorbic acid. The organic acids may include citric acid. The chelating effect of citric acid traps metal ions and the like present in excreta, allowing their removal, and the washing effect of citric acid can potentially provide a high fouling component-removal effect. The pH will vary depending on the water temperature, where the pH in one or more embodiments is the pH measured at an aqueous solution temperature of 20° C. The inorganic acid concentration of the inorganic acid aqueous solution is not particularly restricted so long as the pH of the inorganic acid aqueous solution is no higher than 2.5, but when the inorganic acid is sulfuric acid, the sulfuric acid concentration may be 0.1 mass % to 0.5 mass %. The organic acid concentration of the organic acid aqueous solution is also not particularly restricted so long as the pH of the organic acid aqueous solution is no higher than 2.5, but when the organic acid is citric acid, the citric acid concentration may be 2 mass % to 4 mass %.

The treatment temperature in the inactivating step S31 of one or more embodiments, i.e. the temperature of the aqueous solution containing the inactivating agent, is not particularly restricted so long as the inactivation reaction proceeds. The treatment temperature may be room temperature or higher than room temperature, and it may be 15 to 30° C., for example. The treatment time in the inactivating step S31, i.e. the time for immersing the front sheets, back sheets and absorbent body materials in the aqueous solution containing the inactivating agent, is not particularly restricted so long as the superabsorbent polymer is inactivated and dewatered, and it may be 2 to 60 minutes, for example, and may be 5 to 30 minutes. The amount of aqueous solution in the inactivating step S31, i.e. the amount of the aqueous solution containing the inactivating agent, is not particularly restricted so long as the inactivation reaction proceeds. The amount of the aqueous solution may be 300 to 3000 parts by mass. The amount of the aqueous solution may be 500 to 2500 parts by mass. The amount of the aqueous solution may be 1000 to 2000 parts by mass with respect to 100 parts by mass of the used absorbent articles.

In the first separating step S32 of one or more embodiments, the front sheets (nonwoven fabrics) and back sheets (films) are separated from the mixture containing the pulp fibers, the inactivated superabsorbent polymer and the waste water that has been discharged from the superabsorbent polymer by inactivation. The waste water is water released from the superabsorbent polymer by dewatering with the aqueous solution containing the inactivating agent in the inactivating step S31, or in other words, waste water that includes liquid from excreta and water from the warm water.

The method one or more embodiments for separating the front sheets and back sheets from the pulp fibers, superabsorbent polymer and waste water in the first separating step S32 is not particularly restricted. For example, the products of the inactivating step (front sheets, back sheets, pulp fibers, superabsorbent polymer, waste water, etc.) may be discharged while passing through a screen with a mesh opening of 5 to 100 mm, and for example, a mesh opening of 10 to 60 mm. This will allow the pulp fibers, superabsorbent polymer and waste water to be left in the drainage while the front sheets and back sheets remain on the screen, thereby separating them. Other large matter such as nonwoven fabrics and films may also remain on the screen. In particular, since the superabsorbent polymer is in a highly viscous state before inactivation, separation of the superabsorbent polymer adhering to the front sheets, back sheets and pulp fibers is by no means easy. After inactivation, however, the superabsorbent polymer is in a state of low viscosity due to the dewatering, and therefore the superabsorbent polymer adhering to the front sheets, back sheets and pulp fibers can be easily separated from the front sheets, back sheets and pulp fibers. Therefore, the structural members of the absorbent articles can be efficiently separated and recovered.

For one or more embodiments, the separating step S3 may further include a second separating step S33 of removing the adhesive at the joining sections between the films and other members by a solvent that dissolves the adhesive at the joining sections. For one or more embodiments, the adhesive at the joining sections between the films, nonwoven fabrics and absorbent body materials is removed by a solvent that dissolves the adhesive at the joining sections.

In the second separating step S33 of one or more embodiments, the adhesive at the joining sections between the films (back sheets) and the other members (the nonwoven fabrics of the front sheets, and the absorbent body materials of the absorbent bodies remaining on the surfaces of the front sheets and back sheets) is removed by a solvent. This allows the films and other members to be separated from each other while maintaining their shapes without breaking up. The structural members, such as films, of the absorbent articles can therefore be efficiently recovered. Moreover, since the films and other members can be separated without leaving the adhesive in the films, the films can be reused as highly pure resins. This can minimize adverse effects of the adhesive when the films are reutilized. This description for films also applies to nonwoven fabrics.

The solvent to be used in the second separating step S33 of one or more embodiments is not particularly restricted so long as it can dissolve the adhesive, and examples include terpenes including at least one of terpene hydrocarbons, terpene aldehydes and terpene ketones. In this step, a terpene-containing aqueous solution is used, with the terpene concentration of the aqueous solution being between 0.05 mass % and 2 mass %, for example. The concentration may be 0.075 to 1 mass %. If the terpene concentration is too low, it may not be possible to dissolve the adhesive at the joining sections. Cost may increase if the terpene concentration is too high, on the other hand. The terpene not only dissolves the adhesive, such as a hot-melt adhesive, but also has a washing effect on contaminating oils. Therefore, when printing or the like is present on the structural members of the absorbent articles, such as their back sheets, the terpene can also decompose and remove the printing ink.

Terpene hydrocarbons include myrcene, limonene, pinene, camphor, sabinene, phellandrene, paracymene, ocimene, terpinene, carene, zingiberene, caryophyllene, bisabolene and cedrene. Limonene, pinene, terpinene and carene may be used as the terpene hydrocarbons among these. Examples of terpene aldehydes include citroneral, citral, cyclocitral, safranal, phellandral, perillaldehyde, geranial and neral. Examples of terpene ketones include camphor and thujone. Terpene hydrocarbons may be terpenes. Terpene hydrocarbons may be limonene. Limonenes are of three types: d-limonene, l-limonene and dipentene (dl-limonene), and all of them are suitable for use. A single type of terpene may be used, or two or more may be used in combination.

The treatment temperature in the second separating step S33 of one or more embodiments, i.e. the temperature of the aqueous solution containing the solvent, is not particularly restricted so long as dissolution of the adhesive proceeds to disintegrate the used absorbent articles into its structural members. The treatment temperature may be room temperature or higher than room temperature, and it may be 15 to 30° C., for example. The treatment time in the second separating step S33, i.e. the time for immersion of the front sheets, back sheets and absorbent body materials in the aqueous solution containing the solvent, is not particularly restricted so long as dissolution of the adhesive proceeds to disintegrate the used absorbent articles into its structural members. The treatment time may be 2 to 60 minutes, for example, and may be 5 to 30 minutes. The amount of aqueous solution in the second separating step S33, i.e. the amount of the aqueous solution containing the solvent, is not particularly restricted so long as dissolution of the adhesive proceeds to disintegrate the used absorbent articles into their structural members. The amount of the aqueous solution may be 300 to 3000 parts by mass, for example, and may 500 to 2500 parts by mass. The amount of the aqueous solution may be 100 parts by mass of the used absorbent articles. The amount of adhesive remaining on the films, nonwoven fabrics and absorbent body materials after the second separating step S33 can be limited to no greater than 1 mass % with respect to the films, nonwoven fabrics and absorbent body materials.

In one or more embodiments, the second separating step S33 is carried out in tandem with the inactivating step S31. That is, the superabsorbent polymer adhering to the front sheets, back sheets and pulp fibers may be inactivated while dissolving the adhesive adhering to the front sheets, back sheets and pulp fibers. In this case, the aqueous solution used to immerse the front sheets, back sheets, pulp fibers and superabsorbent polymer may be an aqueous solution containing both the inactivating agent and the solvent. This will allow the back sheets (films), front sheets (nonwoven fabrics) and absorbent bodies (pulp fibers and superabsorbent polymer) to be in an essentially separated state in the aqueous solution during the inactivating step S31. In addition, it will allow separation of the back sheets (films), front sheets (nonwoven fabrics) and absorbent bodies (pulp fibers and superabsorbent polymer) in the subsequent first separating step S32, so that the second separating step S33 can be omitted. In this case, the back sheets (films) and front sheets (nonwoven fabrics) are essentially separated by removal of the adhesive.

For one or more embodiments, the separating step S3 may further include, after the step of removing the adhesive at the joining sections, a first drying step S34 of heat-drying the films, i.e. drying them to remove the solvent by an atmosphere at higher temperature than room temperature, or by hot air. For one or more embodiments, the nonwoven fabrics are also dried in this step.

Sterilization is extremely important for reutilization of used absorbent articles of one or more embodiments. In the first drying step S34, a step of drying the separated films (back sheets) and nonwoven fabrics (front sheets) with a high-temperature atmosphere or hot air is carried out. The drying temperature may be 105 to 210° C., for example, and may be 110 to 190° C. The drying time will differ depending on the drying temperature, but it may be 10 to 120 minutes, for example, and may be 15 to 100 minutes. This will not only allow vaporizing removal of the residual solvent on the surfaces of the films and nonwoven fabrics, but will also allow sterilization of the films and nonwoven fabrics by the high-temperature atmosphere or hot air. The solvent can thus be removed while providing a sterilizing (disinfecting) effect. The films and nonwoven fabric as structural members of the absorbent articles can therefore be efficiently recovered. Because the films and nonwoven fabrics are distinctly different in their density and other properties, they can be easily sorted. The recovered films and nonwoven fabrics can also be regenerated into pellets, for example, and further regenerated into plastic bags and films. Since the amount of adhesive remaining in the recovered films and nonwoven fabrics is no greater than 1 mass % with respect to the films and nonwoven fabrics, the amount of adhesive remaining in the pellets, plastic bags or films can also be no greater than 1 mass % with respect to the pellets, plastic bags or films.

The separating step S3 of one or more embodiments may also include a third separating step S35 of separating the pulp fibers from the separated mixture, and an oxidizing agent treatment step S36 of treating the separated pulp fibers with an aqueous solution that includes an oxidizing agent, to reduce a molecular weight of the residual superabsorbent polymer in the pulp fibers, thereby solubilizing and removing the residual superabsorbent polymer in the pulp fibers.

In one or more embodiments, the method of separating the pulp fibers from the separated mixture (including pulp fibers, superabsorbent polymer and waste water) in the third separating step S35 is not particularly restricted, and for example, the separated mixture may be discharged while passing through a screen with a mesh opening of 0.1 to 4 mm. The mesh opening may be 0.15 to 2 mm. This will allow the superabsorbent polymer and waste water to be left in the drainage while the pulp fibers (residual superabsorbent polymer on the surfaces) remain on the screen, thereby separating the pulp fibers from the mixture. The pulp fibers include numerous impurities, but they can be reutilized depending on the purpose.

In the oxidizing agent treatment step S36 of one or more embodiments, the inactivated superabsorbent polymer remaining on the surfaces of the separated pulp fibers is oxidatively decomposed with an oxidizing agent, thus being reduced in molecular weight and solubilized, and is removed from the surfaces of the pulp fibers. The oxidatively decomposed, molecular weight-reduced and solubilized state of the superabsorbent polymer means a state in which it passes through a 2 mm screen. This allows removal of the impurities such as superabsorbent polymer in the pulp fibers, to produce pulp fibers with a high level of purity. The oxidizing agent treatment can also accomplish secondary sterilization, bleaching and deodorization of the pulp fibers.

The oxidizing agent of one or more embodiments is not particularly restricted so long as it can oxidatively decompose, reduce in molecular weight and solubilize the inactivated superabsorbent polymer, and examples include chlorine dioxide, ozone and sodium hypochlorite. Ozone may be used as the oxidizing agent among these from the viewpoint of high decomposition performance and bleaching performance. When ozone is used as the oxidizing agent, the oxidizing agent treatment may be carried out by contacting the mixture containing the pulp fibers and superabsorbent polymer with the ozone, or more specifically, the ozone may be blown into the drainage containing the pulp fibers and the superabsorbent polymer. Ozone can be generated using, for example, an ozone water generator (such as an ED-OWX-2 ozone water exposure tester by EcoDesign, Inc. or an OS-25V ozone generator by Mitsubishi Electric Corp.).

When ozone is to be blown into drainage containing the pulp fibers and superabsorbent polymer, the ozone concentration in the drainage is not particularly restricted so long as it is a concentration allowing decomposition of the superabsorbent polymer, and it may be 1 to 50 ppm by mass, for example, and may be 2 to 40 ppm by mass. If the concentration is too low, it may not be possible to completely solubilize the superabsorbent polymer, potentially leading to residue of the superabsorbent polymer in the pulp fibers. If the concentration is too high, conversely, the oxidizing power will increase, potentially damaging the pulp fibers and possibly becoming hazardous. The ozone treatment temperature is not particularly restricted so long as it is a temperature allowing decomposition of the superabsorbent polymer, and it may be room temperature, or higher than room temperature, for example. The ozone treatment time is also not particularly restricted so long as it is a time allowing decomposition of the superabsorbent polymer, and it may be 10 to 120 minutes, for example, and may be 20 to 100 minutes. The time may be short if the ozone concentration is high, but it must be a longer time if the ozone concentration is low. When ozone is to be blown into drainage containing the pulp fibers and inactivated superabsorbent polymer, the drainage may be acidic. For example, the pH of the drainage is no higher than 2.5. The pH of the drainage may be 1.5 to 2.4. Treatment in an acidic state can improve the superabsorbent polymer-decomposing and removal effect of the ozone, allowing the superabsorbent polymer to be decomposed in a shorter time.

For one or more embodiments, the separating step S3 may further include a fourth separating step S37 of separating the pulp fibers that have been treated with the oxidizing agent-containing aqueous solution from the oxidizing agent-containing aqueous solution, and a second drying step S38 of drying the separated pulp fibers.

In one or more embodiments, the method of separating the pulp fibers from the oxidizing agent-containing aqueous solution in the fourth separating step S37 is not particularly restricted, and it may be a method in which the treatment solution containing the pulp fibers is passed through a screen with a mesh opening of 0.15 to 2 mm, for example. If the treatment solution containing the pulp fibers is passed through a screen with a mesh opening of 0.15 to 2 mm, the drainage containing the product of oxidative decomposition of the superabsorbent polymer will pass through the screen while the pulp fibers will remain on the screen.

In the subsequent second drying step S38 of one or more embodiments, the pulp fibers that are treated using the oxidizing agent-containing aqueous solution and separated are dried with a high-temperature atmosphere or hot air. The drying temperature may be 105 to 210° C., for example, and may be 110 to 190° C. The drying time will differ depending on the drying temperature, but it may be 10 to 120 minutes, for example, and may be 15 to 100 minutes. This will allow the residual solvent on the surfaces of the pulp fibers to be vaporized and removed, so that highly pure pulp fibers with a very low superabsorbent polymer mixing ratio can be recovered. The structural members of the absorbent articles can therefore be efficiently recovered. The pulp fibers can also be sterilized (disinfected) by the high-temperature atmosphere or hot air.

According to one or more embodiments, the pretreatment step S1 can convert the used absorbent articles into a highly expanded state with water while they are in their original state without breakup, and also without inactivation of the superabsorbent polymer. This can produce extremely high internal pressure in the used absorbent articles, so that some of the locations on the surfaces are in a state prone to rupture. Furthermore, by applying physical shock to the used absorbent articles that are in this state in the disintegration step S2, some of the locations on the surfaces can be torn, allowing the absorbent body materials inside them to effuse outward. This allows the used absorbent articles to disintegrate into at least the films (back sheets) and absorbent body materials. Since the films essentially maintain their original shapes during this time, they can be easily separated from the absorbent body materials in the subsequent separating step S3. This will allow the structural members such as films to be separated from the other structural members while maintaining their shapes without breaking up. Therefore, the structural members of the absorbent articles can be efficiently recovered.

In one or more embodiments, a terpene is used to remove the adhesive, thereby allowing hot-melt adhesive bonding the structural members of the absorbent article to be dissolved at ordinary temperature. The absorbent articles can therefore be easily and cleanly dispersed, the pulp fibers and superabsorbent polymer can be separated from the absorbent articles, and the nonwoven fabrics and films can be separated while retaining the forms of each of the separate members. That is, it is possible to easily recover pulp fibers, films and nonwoven fabrics separately, without crushing the absorbent articles and without a complex separating step. When limonene is used as the terpene, a secondary effect of the limonene provides a refreshing, citrus-like odor and can therefore mask odors from excreta to some extent, reducing the burden of odors on operating personnel and the effect of odors on the surroundings. Since limonene is a monoterpene and has a structure similar to styrene, it can dissolve styrene-based hot-melt adhesives that are commonly used in absorbent articles. Since washing treatment of absorbent articles is possible at ordinary temperature, energy costs can be reduced and diffusion of odors can be minimized. Terpenes have a high washing effect for contaminating oils, and in addition to its dissolving effect for the hot-melt adhesive, it can also decompose and remove printing inks that may be present in printed matter on films, and therefore also allows recovery of printed films as highly pure plastic materials.

If an organic acid aqueous solution with a pH of no higher than 2.5 has been used for inactivation of the superabsorbent polymer, the pulp fibers are unlikely to suffer degradation. When citric acid is used as the organic acid, the chelating effect and washing power of the citric acid can potentially provide an effect of removing fouling components from excreta. A sterilizing effect and a deodorant effect against alkaline odors may also be expected.

Furthermore, by decomposing and removing the superabsorbent polymer of one or more embodiments with an oxidizing agent, it is possible to prevent contamination of the pulp fibers or drastic increase in waste water due to water absorption by the superabsorbent polymer. By adjusting the type and concentration of oxidizing agent used, it is possible to simultaneously carry out oxidative decomposition and sterilization of the superabsorbent polymer. When an oxidizing agent treatment step is not provided, or ozone is used as the oxidizing agent in the oxidizing agent treatment step, absolutely no chlorine-based agents are used and therefore high-quality RPF production can be carried out from the recovered plastic members while avoiding damage to the furnace. If the films are sorted out and recovered, they can be reused as raw material for bags or films. Since no salts are used during the treatment steps, there is no residue in the pulp fibers and high quality pulp with a low ash content can be recovered.

Incidentally, the superabsorbent polymer of one or more embodiments may be recovered from the drainage containing the superabsorbent polymer and waste water separated by the third separating step S35. The recovering method is not particularly restricted and may be a method using a screen, for example, while the method of restoring the water-absorbing capacity of the recovered water-absorbent polymer may be a method of treatment with an aqueous alkali metal salt solution, for example. The residual drainage (with ozone dissolved in a trace amount of 10 ppm), which has been separated by the fourth separating step S37, may be circulated back to the pretreatment step S1. This allows the ozone-containing drainage to be used in a non-wasteful manner, and allows the pretreatment in the pretreatment step S1 and sterilization with the ozone to be carried out simultaneously.

The method of one or more embodiments can be suitably used for recovery of individual structural members such as films and absorbing members from used absorbent articles.

One or more embodiments have been described assuming a film as the structural member of the back sheet and a nonwoven fabric as the structural member of the front sheet. However, embodiments wherein a nonwoven fabric is the structural member of the back sheet and a film is the structural member of the front sheet, or wherein films are the structural members of both the back sheet and the front sheet, may also be carried out by the same method as the embodiment described above, and can exhibit the same function and effect.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1 Used absorbent article
2 Front sheet
3 Back sheet
4 Absorbent body
S1 Pretreatment step
S2 Disintegration step
S3 Separating step

What is claimed is:

1. A method of recovering structural members from a used absorbent article comprising a front sheet, a back sheet, and an absorbent body between the front sheet and the back sheet, wherein at least one of the front sheet and the back sheet comprises a film, and wherein the absorbent body comprises an absorbent body material including a superabsorbent polymer and pulp fibers, the method comprising:
   swelling the used absorbent article with water;
   applying a physical shock to and disintegrating the swelled used absorbent article into at least the film and the absorbent body material;
   inactivating the superabsorbent polymer in an acidic aqueous solution containing an inactivating agent; and
   after the inactivating of the superabsorbent polymer, separating the film and the absorbent body material,
   wherein in the separating of the film and the absorbent body material, the film is separated from a mixture containing the pulp fibers, the inactivated superabsorbent polymer, and any waste water discharged from the inactivation of the superabsorbent polymer.

2. The method according to claim 1, wherein in the disintegrating of the swelled used absorbent article,
   the swelled used absorbent article is loaded into a horizontal-axis rotary drum, and
   the physical shock is applied to the swelled used absorbent article by rotating the rotary drum, raising the swelled used absorbent article from a lower area that is further downward in a vertical direction inside the rotary drum to an upper area that is further upward, and allowing the swelled used absorbent article to fall by gravity from the upper area to the lower area and physically impact an inner wall of the rotary drum in the lower area.

3. The method according to claim 2, wherein in the swelling of the used absorbent article, the water is at a temperature of 70° C. to 98° C.

4. The method according to claim 2, wherein the swelled used absorbent article contains the water in an amount of 90 mass % or greater of a maximum absorption of the used absorbent article.

5. The method according to claim 2, wherein the film and the absorbent body material are connected at joining sections by an adhesive, and
   wherein in the separating of the film and the absorbent body material, the adhesive at the joining sections is removed by dissolving the adhesive with a solvent.

6. The method according to claim 5, wherein the solvent comprises at least one terpene selected from a group consisting of terpene hydrocarbon, terpene aldehyde and terpene ketone.

7. The method according to claim 1, wherein in the swelling of the used absorbent article, the water is at a temperature between 70° C. to 98° C.

8. The method according to claim 1, wherein the swelled used absorbent article contains the water in an amount of 90 mass % or greater of a maximum absorption of the used absorbent article.

9. The method according to claim 1, wherein in the separating of the film and the absorbent body material,
the pulp fibers are separated from the separated mixture, and
the separated pulp fibers are treated with an aqueous solution of an oxidizing agent,
wherein the oxidizing agent reduces a molecular weight of any residual superabsorbent polymer remaining in the pulp fibers, thereby solubilizing and removing the residual superabsorbent polymer.

10. The method according to claim 1, wherein the used absorbent article is at least one selected from a group consisting of a paper diaper, a urine-absorbing pad, a sanitary napkin, a bed sheet and a pet sheet.

11. The method according to claim 1, wherein the film and the absorbent body material are connected at joining sections by an adhesive, and
wherein in the separating of the film and the absorbent body material, the adhesive at the joining sections is removed by dissolving the adhesive with a solvent.

12. The method according to claim 11, wherein the solvent comprises at least one terpene selected from a group consisting of terpene hydrocarbon, terpene aldehyde and terpene ketone.

13. The method according to claim 11, wherein in the separating of the film and the absorbent body material, the film is heat-dried to remove the solvent, after the adhesive at the joining sections has been removed.

14. A method of recovering structural members from a used absorbent article comprising a front sheet, a back sheet, and an absorbent body between the front sheet and the back sheet, wherein at least one of the front sheet and the back sheet comprises a film, and wherein the absorbent body comprises an absorbent body material, the method comprising:
swelling the used absorbent article with water;
applying a physical shock to and disintegrating the swelled used absorbent article into at least the film and the absorbent body material; and
separating the film and the absorbent body material,
wherein the film and the absorbent body material are connected at joining sections by an adhesive, and
wherein in the separating of the film and the absorbent body material, the adhesive at the joining sections is removed by dissolving the adhesive with a solvent.

15. The method according to claim 14, wherein the solvent comprises at least one terpene selected from a group consisting of terpene hydrocarbon, terpene aldehyde and terpene ketone.

16. The method according to claim 14, wherein in the separating of the film and the absorbent body material, the film is heat-dried to remove the solvent, after the adhesive at the joining sections has been removed.

* * * * *